(12) United States Patent
Tanaka et al.

(10) Patent No.: US 8,026,063 B2
(45) Date of Patent: Sep. 27, 2011

(54) METHOD OF EXAMINING INFLAMMATORY DISEASE AND METHOD OF SCREENING REMEDY FOR IMFLAMMATORY DISEASE

(75) Inventors: Toshihiro Tanaka, Yokohama (JP); Koichi Ozaki, Yokohama (JP); Aritoshi Iida, Yokohama (JP); Masatsugu Hori, Suita (JP); Yusuke Nakamura, Yokohama (JP)

(73) Assignee: Riken, Saitama (JP)

( * ) Notice: Subject to any disclaimer, the term of this patent is extended or adjusted under 35 U.S.C. 154(b) by 534 days.

(21) Appl. No.: 11/795,016

(22) PCT Filed: Jan. 11, 2006

(86) PCT No.: PCT/JP2006/300224
§ 371 (c)(1),
(2), (4) Date: Feb. 4, 2008

(87) PCT Pub. No.: WO2006/075626
PCT Pub. Date: Jul. 20, 2006

(65) Prior Publication Data
US 2008/0280293 A1 Nov. 13, 2008

(30) Foreign Application Priority Data
Jan. 11, 2005 (JP) ................ 2005-004297

(51) Int. Cl.
*C12Q 1/68* (2006.01)
(52) U.S. Cl. ...................................... 435/6.1
(58) Field of Classification Search .......... None
See application file for complete search history.

(56) References Cited

U.S. PATENT DOCUMENTS 6,812,339 B1* 11/2004 Venter et al. ............ 536/24.31
6,900,016 B1* 5/2005 Venter et al. ............ 435/6
2006/0141493 A1* 6/2006 West et al. ............ 435/6

FOREIGN PATENT DOCUMENTS

JP 2002-136291 A 5/2002

OTHER PUBLICATIONS

Edfeldt et al., "Expression of Toll-like receptors in human atherosclerotic lesions and the relevance to myocardial infaction," European Heart Journal, vol. 24, 2003, pp. 156.

Hamann et al., "Rapid and inexpensive real-time PCR for genotyping functional polymorphisms within the Toll-like receptor -2, -4, and -9 genes," J. Immunol. Methods., vol. 285, No. 2, 2004, pp. 281-291.
Barber et al., "TLR4 and TNF-alpha polymorphisms are associated with an increased risk for severe sepsis following burn injury," J. Med Genet, vol. 41, No. 11, 2004, pp. 808-813.
Hallman et al., "Toll-like receptors as sensors of pathogens," Pediatr. Res., vol. 50, No. 3, 2001, pp. 315-321.
Anders et al., "Signaling danger: toll-like receptors and their potential roles in kidney disease," J. Am. Soc. Nephrol., vol. 15, No. 4, 2004, pp. 854-867.
Ozaki et al., "Taikeiteki SNP Kaiseki ni yoru Shinkinkosoku Kanjusei Idenshigun no Dotei to sono Kinokaiseki, Lymphotoxin-α oyobi sono Ketsugobunshi Galectin-2 to Shinkinkosoku," Protein, Nucleic acid and Enzyme, vol. 49, No. 14, 2004, pp. 2215-2221.
Ozaki et al., "Tainshi ldenbyo to shite no JUunkanki Shikkan Shinkinkosoku," Saishin Igaku, vol. 60, September issue, 2005, pp. 2026-2034.
Breslow, Jan L., Cardiovascular disease burden increases, NIH funding decreases, Nature Medicine, vol. 3, No. 6, Jun. 1997, pp. 600-601.
Braunwald, Eugene, M.D., Shattuck Lecture—Cardiovascular Medicine at the Turn of the Millennium: Triumphs, Concerns, and Opportunities, The New England Journal of Medicine, vol. 337, No. 19, pp. 1360-1369 Nov. 6, 1997.
Gitt, Michael A., et al., Galectin-2, Galectins-5 and -9, and Galectins-4 and -6, Trends in Glycoscience and Glycotechnology, vol. 9, No. 45, pp. 87-93, Jan. 1997.
Akira, Shizuo, Toll-like Receptor Signaling, The Journal of Biological Chemistry, vol. 278, No. 40, pp. 38105-38108, Oct. 3, 2003.
Tantisira, K., et al., Toll-like receptor 6 gene (TLR6): singlenucleotide polymorphism frequencies and preliminary association with the diagnosis of asthma, Genes and Immunity, vol. 5, pp. 343-346, 2004.
Ozaki, Kouichi et al., Functional variation in LGAS2 confers risk of myocardial infarction and regulates lymphotoxin-α secretion in vitro, Nature, vol. 429, pp. 72-75, May 6, 2004.

* cited by examiner

*Primary Examiner* — Kenneth R. Horlick
*Assistant Examiner* — David Thomas
(74) *Attorney, Agent, or Firm* — Birch, Stewart, Kolasch & Birch, LLP

(57) ABSTRACT

A gene polymorphism on a Toll-like receptor gene is analyzed and an inflammatory disease is examined based on the results of the analysis. A remedy for an inflammatory disease is screened by selecting a substance capable of altering the interaction between Toll-like receptor and galectin-2.

1 Claim, 1 Drawing Sheet

SEQUENCE LISTING

<160> NUMBER OF SEQ ID NOS: 22

<210> SEQ ID NO 1
<211> LENGTH: 401
<212> TYPE: DNA
<213> ORGANISM: Homo sapiens

<400> SEQUENCE: 1
tgtcaaaaat atagaccaag tatcaagtga agtgttagag ggctggcctg attcttataa    60
gtgtgactac ccggaaagtt atagaggaac cctactaaag gactttcaca tgtctgaatt   120
atcctgcaac ataactctgc tgatcgtcac catcgttgcc accatgctgg tgttggctgt   180
gactgtgacc tccctctgca kctacttgga tctgccctgg tatctcagga tggtgtgcca   240
gtggacccag acccggcgca gggccaggaa catacccttta gaagaactcc aaagaaatct   300
ccagtttcat gcatttattt catatagtgg gcacgattct ttctgggtga agaatgaatt   360
attgccaaac ctagagaaag aaggtatgca gatttgcctt c                       401

<210> SEQ ID NO 2
<211> LENGTH: 404
<212> TYPE: DNA
<213> ORGANISM: Homo sapiens

<400> SEQUENCE: 2
aatctgtatc tgtatcaaga tgatctgaag aacagcttct acctttagga atgtctagtg    60
ttccaaaatg actagcatct tccattttgc cattatcttc atgttaatac ttcagatcag   120
aatacaatta tctgaagaaa gtgaattttt agttgatagg tcaaaaaacg gtctcatcca   180
cgttcctaaa gacctaycccc agaaaacaac aatcttaaat atatcgcaaa attatatatc   240
tgagctttgg acttctgaca tcttatcact gtcaaaactg aggattttga taatttctca   300
taatagaatc cagtatcttg atatcagtgt tttcaaattc aaccaggaat tggaatactt   360
ggatttgtcc cacaacaagt tggtgaagat ttcttgccac ccta                    404

<210> SEQ ID NO 3
<211> LENGTH: 403
<212> TYPE: DNA
<213> ORGANISM: Homo sapiens

<400> SEQUENCE: 3
gttttacgta agttagctta attcagtaat tcaaaacaca tgcgattatc ttcgttttaa    60
agaccagaaa actaaaggtt ggtaggtttg tataatttga ctaccattgc gtatctttat   120
tttaatacat tttataaatg caagcttctg ctatgattaa aagtgattac cacattttac   180
agaccagaaa gtaataataa gygttggtga agatgtgaaa aaatgagaac tcctgtacac   240
catttgtggg aatgtaaaat ggtacagatg ctgtggagaa tcatatggtg ggtgctcaaa   300
aaattaaaaa tagatttacc acatgatcca gcaatctcac ttctgagtac gtatccaaaa   360
gaattgaaaa cagagacttt aagagatatt tgtacaacca tgt                     403

<210> SEQ ID NO 4
<211> LENGTH: 22
<212> TYPE: DNA
<213> ORGANISM: Artificial sequence
<220> FEATURE:
<223> OTHER INFORMATION: primer

<400> SEQUENCE: 4

```
gtgtgactac ccggaaagtt at                                              22

<210> SEQ ID NO 5
<211> LENGTH: 23
<212> TYPE: DNA
<213> ORGANISM: Artificial sequence
<220> FEATURE:
<223> OTHER INFORMATION: primer

<400> SEQUENCE: 5
gataccaggg cagatccaag tag                                             23

<210> SEQ ID NO 6
<211> LENGTH: 21
<212> TYPE: DNA
<213> ORGANISM: Artificial sequence
<220> FEATURE:
<223> OTHER INFORMATION: primer

<400> SEQUENCE: 6
ccaaaagaat gtagcctcca c                                               21

<210> SEQ ID NO 7
<211> LENGTH: 22
<212> TYPE: DNA
<213> ORGANISM: Artificial sequence
<220> FEATURE:
<223> OTHER INFORMATION: primer

<400> SEQUENCE: 7
ttaaagtctt gaaggccctc ag                                              22

<210> SEQ ID NO 8
<211> LENGTH: 26
<212> TYPE: DNA
<213> ORGANISM: Artificial sequence
<220> FEATURE:
<223> OTHER INFORMATION: primer

<400> SEQUENCE: 8
ggtttgtata atttgactac cattgc                                          26

<210> SEQ ID NO 9
<211> LENGTH: 21
<212> TYPE: DNA
<213> ORGANISM: Artificial sequence
<220> FEATURE:
<223> OTHER INFORMATION: primer

<400> SEQUENCE: 9
tggatacgta ctcagaagtg a                                               21

<210> SEQ ID NO 10
<211> LENGTH: 21
<212> TYPE: DNA
<213> ORGANISM: Artificial sequence
<220> FEATURE:
<223> OTHER INFORMATION: primer

<400> SEQUENCE: 10
agcctccact ttataagtct g                                               21

<210> SEQ ID NO 11
<211> LENGTH: 27
<212> TYPE: DNA
<213> ORGANISM: Artificial sequence
<220> FEATURE:
```

```
<223> OTHER INFORMATION: primer

<400> SEQUENCE: 11
tttgtataat ttgactacca ttgcgta                                              27

<210> SEQ ID NO 12
<211> LENGTH: 2361
<212> TYPE: DNA
<213> ORGANISM: Homo sapiens
<220> FEATURE:
<221> NAME/KEY: CDS
<222> LOCATION: (1)..(2361)

<400> SEQUENCE: 12 atg act agc atc ttc cat ttt gcc att atc ttc atg tta ata ctt cag      48
Met Thr Ser Ile Phe His Phe Ala Ile Ile Phe Met Leu Ile Leu Gln
1               5                   10                  15 atc aga ata caa tta tct gaa gaa agt gaa ttt tta gtt gat agg tca      96
Ile Arg Ile Gln Leu Ser Glu Glu Ser Glu Phe Leu Val Asp Arg Ser
            20                  25                  30 aaa aac ggt ctc atc cac gtt cct aaa gac cta tcc cag aaa aca aca     144
Lys Asn Gly Leu Ile His Val Pro Lys Asp Leu Ser Gln Lys Thr Thr
        35                  40                  45 atc tta aat ata tcg caa aat tat ata tct gag ctt tgg act tct gac     192
Ile Leu Asn Ile Ser Gln Asn Tyr Ile Ser Glu Leu Trp Thr Ser Asp
    50                  55                  60 atc tta tca ctg tca aaa ctg agg att tta ata ttt tct cat aat aga     240
Ile Leu Ser Leu Ser Lys Leu Arg Ile Leu Ile Ile Ser His Asn Arg
65                  70                  75                  80 atc cag tat ctt gat atc agt gtt ttc aaa ttc aac cag gaa ttg gaa     288
Ile Gln Tyr Leu Asp Ile Ser Val Phe Lys Phe Asn Gln Glu Leu Glu
                85                  90                  95 tac ttg gat ttg tcc cac aac aag ttg gtg aag att tct tgc cac cct     336
Tyr Leu Asp Leu Ser His Asn Lys Leu Val Lys Ile Ser Cys His Pro
            100                 105                 110 act gtg aac ctc aag cac ttg gac ctg tca ttt aat gca ttt gat gcc     384
Thr Val Asn Leu Lys His Leu Asp Leu Ser Phe Asn Ala Phe Asp Ala
        115                 120                 125 ctg cct ata tgc aaa gag ttt ggc aat atg tct caa cta aaa ttt ctg     432
Leu Pro Ile Cys Lys Glu Phe Gly Asn Met Ser Gln Leu Lys Phe Leu
    130                 135                 140 ggg ttg agc acc aca cac tta gaa aaa tct agt gtg ctg cca att gct     480
Gly Leu Ser Thr Thr His Leu Glu Lys Ser Ser Val Leu Pro Ile Ala
145                 150                 155                 160 cat ttg aat atc agc aag gtc ttg ctg gtc tta gga gag act tat ggg     528
His Leu Asn Ile Ser Lys Val Leu Leu Val Leu Gly Glu Thr Tyr Gly
                165                 170                 175 gaa aaa gaa gac cct gag ggc ctt caa gac ttt aac act gag agt ctg     576
Glu Lys Glu Asp Pro Glu Gly Leu Gln Asp Phe Asn Thr Glu Ser Leu
            180                 185                 190 cac att gtg ttc ccc aca aac aaa gaa ttc cat ttt att ttg gat gtg     624
His Ile Val Phe Pro Thr Asn Lys Glu Phe His Phe Ile Leu Asp Val
        195                 200                 205 tca gtc aag act gta gca aat ctg gaa cta tct aat atc aaa tgt gtg     672
Ser Val Lys Thr Val Ala Asn Leu Glu Leu Ser Asn Ile Lys Cys Val
    210                 215                 220 cta gaa gat aac aaa tgt tct tac ttc cta agt att ctg gcg aaa ctt     720
Leu Glu Asp Asn Lys Cys Ser Tyr Phe Leu Ser Ile Leu Ala Lys Leu
225                 230                 235                 240 caa aca aat cca aag tta tca agt ctt acc tta aac aac att gaa aca     768
Gln Thr Asn Pro Lys Leu Ser Ser Leu Thr Leu Asn Asn Ile Glu Thr
                245                 250                 255
```

| | | | | | | | | | | | | | | | | |
|---|---|---|---|---|---|---|---|---|---|---|---|---|---|---|---|---|
| act | tgg | aat | tct | ttc | att | agg | atc | ctc | cag | ctg | gtt | tgg | cat | aca | act | 816 |
| Thr | Trp | Asn | Ser 260 | Phe | Ile | Arg | Ile | Leu 265 | Gln | Leu | Val | Trp | His 270 | Thr | Thr | |
| gta | tgg | tat | ttc | tca | att | tca | aac | gtg | aag | cta | cag | ggt | cag | ctg | gac | 864 |
| Val | Trp | Tyr 275 | Phe | Ser | Ile | Ser | Asn 280 | Val | Lys | Leu | Gln | Gly 285 | Gln | Leu | Asp | |
| ttc | aga | gat | ttt | gat | tat | tct | ggc | act | tcc | ttg | aag | gcc | ttg | tct | ata | 912 |
| Phe | Arg | Asp | Phe 290 | Asp | Tyr | Ser | Gly | Thr 295 | Ser | Leu | Lys | Ala | Leu 300 | Ser | Ile | |
| cac | caa | gtt | gtc | agc | gat | gtg | ttc | ggt | ttt | ccg | caa | agt | tat | atc | tat | 960 |
| His 305 | Gln | Val | Val | Ser | Asp 310 | Val | Phe | Gly | Phe | Pro 315 | Gln | Ser | Tyr | Ile | Tyr 320 | |
| gaa | atc | ttt | tcg | aat | atg | aac | atc | aaa | aat | ttc | aca | gtg | tct | ggt | aca | 1008 |
| Glu | Ile | Phe | Ser | Asn 325 | Met | Asn | Ile | Lys | Asn 330 | Phe | Thr | Val | Ser | Gly 335 | Thr | |
| cgc | atg | gtc | cac | atg | ctt | tgc | cca | tcc | aaa | att | agc | ccg | ttc | ctg | cat | 1056 |
| Arg | Met | Val | His 340 | Met | Leu | Cys | Pro | Ser 345 | Lys | Ile | Ser | Pro | Phe 350 | Leu | His | |
| ttg | gat | ttt | tcc | aat | aat | ctc | tta | aca | gac | acg | gtt | ttt | gaa | aat | tgt | 1104 |
| Leu | Asp | Phe | Ser 355 | Asn | Asn | Leu | Leu | Thr 360 | Asp | Thr | Val | Phe | Glu 365 | Asn | Cys | |
| ggg | cac | ctt | act | gag | ttg | gag | aca | ctt | att | tta | caa | atg | aat | caa | tta | 1152 |
| Gly | His | Leu | Thr 370 | Glu | Leu | Glu | Thr | Leu 375 | Ile | Leu | Gln | Met | Asn 380 | Gln | Leu | |
| aaa | gaa | ctt | tca | aaa | ata | gct | gaa | atg | act | aca | cag | atg | aag | tct | ctg | 1200 |
| Lys 385 | Glu | Leu | Ser | Lys | Ile 390 | Ala | Glu | Met | Thr | Thr 395 | Gln | Met | Lys | Ser | Leu 400 | |
| caa | caa | ttg | gat | att | agc | cag | aat | tct | gta | agc | tat | gat | gaa | aag | aaa | 1248 |
| Gln | Gln | Leu | Asp | Ile 405 | Ser | Gln | Asn | Ser | Val 410 | Ser | Tyr | Asp | Glu | Lys 415 | Lys | |
| gga | gac | tgt | tct | tgg | act | aaa | agt | tta | tta | agt | tta | aat | atg | tct | tca | 1296 |
| Gly | Asp | Cys | Ser 420 | Trp | Thr | Lys | Ser | Leu 425 | Leu | Ser | Leu | Asn | Met 430 | Ser | Ser | |
| aat | ata | ctt | act | gac | act | att | ttc | aga | tgt | tta | cct | ccc | agg | atc | aag | 1344 |
| Asn | Ile | Leu | Thr 435 | Asp | Thr | Ile | Phe | Arg 440 | Cys | Leu | Pro | Pro | Arg 445 | Ile | Lys | |
| gta | ctt | gat | ctt | cac | agc | aat | aaa | ata | aag | agc | att | cct | aaa | caa | gtc | 1392 |
| Val | Leu | Asp | Leu | His 450 | Ser | Asn | Lys | Ile | Lys 455 | Ser | Ile | Pro | Lys | Gln 460 | Val | |
| gta | aaa | ctg | gaa | gct | ttg | caa | gaa | ctc | aat | gtt | gct | ttc | aat | tct | tta | 1440 |
| Val 465 | Lys | Leu | Glu | Ala | Leu 470 | Gln | Glu | Leu | Asn | Val 475 | Ala | Phe | Asn | Ser | Leu 480 | |
| act | gac | ctt | cct | gga | tgt | ggc | agc | ttt | agc | agc | ctt | tct | gta | ttg | atc | 1488 |
| Thr | Asp | Leu | Pro | Gly 485 | Cys | Gly | Ser | Phe | Ser 490 | Ser | Leu | Ser | Val | Leu 495 | Ile | |
| att | gat | cac | aat | tca | gtt | tcc | cac | cca | tca | gct | gat | ttc | ttc | cag | agc | 1536 |
| Ile | Asp | His | Asn 500 | Ser | Val | Ser | His | Pro 505 | Ser | Ala | Asp | Phe | Phe 510 | Gln | Ser | |
| tgc | cag | aag | atg | agg | tca | ata | aaa | gca | ggg | gac | aat | cca | ttc | caa | tgt | 1584 |
| Cys | Gln | Lys | Met 515 | Arg | Ser | Ile | Lys | Ala 520 | Gly | Asp | Asn | Pro | Phe 525 | Gln | Cys | |
| acc | tgt | gag | cta | gga | gaa | ttt | gtc | aaa | aat | ata | gac | caa | gta | tca | agt | 1632 |
| Thr | Cys | Glu | Leu 530 | Gly | Glu | Phe | Val | Lys 535 | Asn | Ile | Asp | Gln | Val 540 | Ser | Ser | |
| gaa | gtg | tta | gag | ggc | tgg | cct | gat | tct | tat | aag | tgt | gac | tac | ccg | gaa | 1680 |
| Glu 545 | Val | Leu | Glu | Gly | Trp 550 | Pro | Asp | Ser | Tyr | Lys 555 | Cys | Asp | Tyr | Pro | Glu 560 | |
| agt | tat | aga | gga | acc | cta | cta | aag | gac | ttt | cac | atg | tct | gaa | tta | tcc | 1728 |
| Ser | Tyr | Arg | Gly | Thr 565 | Leu | Leu | Lys | Asp | Phe 570 | His | Met | Ser | Glu | Leu 575 | Ser | |

|  |  |
|---|---|
| tgc aac ata act ctg ctg atc gtc acc atc gtt gcc acc atg ctg gtg<br>Cys Asn Ile Thr Leu Leu Ile Val Thr Ile Val Ala Thr Met Leu Val<br>580 585 590 | 1776 |
| ttg gct gtg act gtg acc tcc ctc tgc atc tac ttg gat ctg ccc tgg<br>Leu Ala Val Thr Val Thr Ser Leu Cys Ile Tyr Leu Asp Leu Pro Trp<br>595 600 605 | 1824 |
| tat ctc agg atg gtg tgc cag tgg acc cag acc cgg cgc agg gcc agg<br>Tyr Leu Arg Met Val Cys Gln Trp Thr Gln Thr Arg Arg Arg Ala Arg<br>610 615 620 | 1872 |
| aac ata ccc tta gaa gaa ctc caa aga aat ctc cag ttt cat gca ttt<br>Asn Ile Pro Leu Glu Glu Leu Gln Arg Asn Leu Gln Phe His Ala Phe<br>625 630 635 640 | 1920 |
| att tca tat agt ggg cac gat tct ttc tgg gtg aag aat gaa tta ttg<br>Ile Ser Tyr Ser Gly His Asp Ser Phe Trp Val Lys Asn Glu Leu Leu<br>645 650 655 | 1968 |
| cca aac cta gag aaa gaa ggt atg cag att tgc ctt cat gag aga aac<br>Pro Asn Leu Glu Lys Glu Gly Met Gln Ile Cys Leu His Glu Arg Asn<br>660 665 670 | 2016 |
| ttt gtt cct ggc aag agc att gtg gaa aat atc atc acc tgc att gag<br>Phe Val Pro Gly Lys Ser Ile Val Glu Asn Ile Ile Thr Cys Ile Glu<br>675 680 685 | 2064 |
| aag agt tac aag tcc atc ttt gtt ttg tct ccc aac ttt gtc cag agt<br>Lys Ser Tyr Lys Ser Ile Phe Val Leu Ser Pro Asn Phe Val Gln Ser<br>690 695 700 | 2112 |
| gaa tgg tgc cat tat gaa ctc tac ttt gcc cat cac aat ctc ttt cat<br>Glu Trp Cys His Tyr Glu Leu Tyr Phe Ala His His Asn Leu Phe His<br>705 710 715 720 | 2160 |
| gaa gga tct aat agc tta atc ctg atc ttg ctg gaa ccc att ccg cag<br>Glu Gly Ser Asn Ser Leu Ile Leu Ile Leu Leu Glu Pro Ile Pro Gln<br>725 730 735 | 2208 |
| tac tcc att cct agc agt tat cac aag ctc aaa agt ctc atg gcc agg<br>Tyr Ser Ile Pro Ser Ser Tyr His Lys Leu Lys Ser Leu Met Ala Arg<br>740 745 750 | 2256 |
| agg act tat ttg gaa tgg ccc aag gaa aag agc aaa cgt ggc ctt ttt<br>Arg Thr Tyr Leu Glu Trp Pro Lys Glu Lys Ser Lys Arg Gly Leu Phe<br>755 760 765 | 2304 |
| tgg gct aac tta agg gca gcc att aat att aag ctg aca gag caa gca<br>Trp Ala Asn Leu Arg Ala Ala Ile Asn Ile Lys Leu Thr Glu Gln Ala<br>770 775 780 | 2352 |
| aag aaa tag<br>Lys Lys<br>785 | 2361 |

<210> SEQ ID NO 13
<211> LENGTH: 786
<212> TYPE: PRT
<213> ORGANISM: Homo sapiens

<400> SEQUENCE: 13

Met Thr Ser Ile Phe His Phe Ala Ile Ile Phe Met Leu Ile Leu Gln
1               5                   10                  15

Ile Arg Ile Gln Leu Ser Glu Glu Ser Glu Phe Leu Val Asp Arg Ser
            20                  25                  30

Lys Asn Gly Leu Ile His Val Pro Lys Asp Leu Ser Gln Lys Thr Thr
        35                  40                  45

Ile Leu Asn Ile Ser Gln Asn Tyr Ile Ser Glu Leu Trp Thr Ser Asp
    50                  55                  60

Ile Leu Ser Leu Ser Lys Leu Arg Ile Leu Ile Ile Ser His Asn Arg
65                  70                  75                  80

-continued

```
Ile Gln Tyr Leu Asp Ile Ser Val Phe Lys Phe Asn Gln Glu Leu Glu
                85                  90                  95
Tyr Leu Asp Leu Ser His Asn Lys Leu Val Lys Ile Ser Cys His Pro
            100                 105                 110
Thr Val Asn Leu Lys His Leu Asp Leu Ser Phe Asn Ala Phe Asp Ala
        115                 120                 125
Leu Pro Ile Cys Lys Glu Phe Gly Asn Met Ser Gln Leu Lys Phe Leu
    130                 135                 140
Gly Leu Ser Thr Thr His Leu Glu Lys Ser Ser Val Leu Pro Ile Ala
145                 150                 155                 160
His Leu Asn Ile Ser Lys Val Leu Leu Val Leu Gly Glu Thr Tyr Gly
                165                 170                 175
Glu Lys Glu Asp Pro Glu Gly Leu Gln Asp Phe Asn Thr Glu Ser Leu
            180                 185                 190
His Ile Val Phe Pro Thr Asn Lys Glu Phe His Phe Ile Leu Asp Val
        195                 200                 205
Ser Val Lys Thr Val Ala Asn Leu Glu Leu Ser Asn Ile Lys Cys Val
    210                 215                 220
Leu Glu Asp Asn Lys Cys Ser Tyr Phe Leu Ser Ile Leu Ala Lys Leu
225                 230                 235                 240
Gln Thr Asn Pro Lys Leu Ser Ser Leu Thr Leu Asn Asn Ile Glu Thr
                245                 250                 255
Thr Trp Asn Ser Phe Ile Arg Ile Leu Gln Leu Val Trp His Thr Thr
            260                 265                 270
Val Trp Tyr Phe Ser Ile Ser Asn Val Lys Leu Gln Gly Gln Leu Asp
        275                 280                 285
Phe Arg Asp Phe Asp Tyr Ser Gly Thr Ser Leu Lys Ala Leu Ser Ile
    290                 295                 300
His Gln Val Val Ser Asp Val Phe Gly Phe Pro Gln Ser Tyr Ile Tyr
305                 310                 315                 320
Glu Ile Phe Ser Asn Met Asn Ile Lys Asn Phe Thr Val Ser Gly Thr
                325                 330                 335
Arg Met Val His Met Leu Cys Pro Ser Lys Ile Ser Pro Phe Leu His
            340                 345                 350
Leu Asp Phe Ser Asn Asn Leu Leu Thr Asp Thr Val Phe Glu Asn Cys
        355                 360                 365
Gly His Leu Thr Glu Leu Glu Thr Leu Ile Leu Gln Met Asn Gln Leu
    370                 375                 380
Lys Glu Leu Ser Lys Ile Ala Glu Met Thr Thr Gln Met Lys Ser Leu
385                 390                 395                 400
Gln Gln Leu Asp Ile Ser Gln Asn Ser Val Ser Tyr Asp Glu Lys Lys
                405                 410                 415
Gly Asp Cys Ser Trp Thr Lys Ser Leu Leu Ser Leu Asn Met Ser Ser
            420                 425                 430
Asn Ile Leu Thr Asp Thr Ile Phe Arg Cys Leu Pro Pro Arg Ile Lys
        435                 440                 445
Val Leu Asp Leu His Ser Asn Lys Ile Lys Ser Ile Pro Lys Gln Val
    450                 455                 460
Val Lys Leu Glu Ala Leu Gln Glu Leu Asn Val Ala Phe Asn Ser Leu
465                 470                 475                 480
Thr Asp Leu Pro Gly Cys Gly Ser Phe Ser Ser Leu Ser Val Leu Ile
                485                 490                 495
Ile Asp His Asn Ser Val Ser His Pro Ser Ala Asp Phe Phe Gln Ser
            500                 505                 510
```

```
Cys Gln Lys Met Arg Ser Ile Lys Ala Gly Asp Asn Pro Phe Gln Cys
            515                 520                 525

Thr Cys Glu Leu Gly Glu Phe Val Lys Asn Ile Asp Gln Val Ser Ser
        530                 535                 540

Glu Val Leu Glu Gly Trp Pro Asp Ser Tyr Lys Cys Asp Tyr Pro Glu
545                 550                 555                 560

Ser Tyr Arg Gly Thr Leu Leu Lys Asp Phe His Met Ser Glu Leu Ser
                565                 570                 575

Cys Asn Ile Thr Leu Leu Ile Val Thr Ile Val Ala Thr Met Leu Val
            580                 585                 590

Leu Ala Val Thr Val Thr Ser Leu Cys Ile Tyr Leu Asp Leu Pro Trp
        595                 600                 605

Tyr Leu Arg Met Val Cys Gln Trp Thr Gln Thr Arg Arg Arg Ala Arg
610                 615                 620

Asn Ile Pro Leu Glu Glu Leu Gln Arg Asn Leu Gln Phe His Ala Phe
625                 630                 635                 640

Ile Ser Tyr Ser Gly His Asp Ser Phe Trp Val Lys Asn Glu Leu Leu
                645                 650                 655

Pro Asn Leu Glu Lys Glu Gly Met Gln Ile Cys Leu His Glu Arg Asn
            660                 665                 670

Phe Val Pro Gly Lys Ser Ile Val Glu Asn Ile Ile Thr Cys Ile Glu
        675                 680                 685

Lys Ser Tyr Lys Ser Ile Phe Val Leu Ser Pro Asn Phe Val Gln Ser
690                 695                 700

Glu Trp Cys His Tyr Glu Leu Tyr Phe Ala His His Asn Leu Phe His
705                 710                 715                 720

Glu Gly Ser Asn Ser Leu Ile Leu Ile Leu Leu Glu Pro Ile Pro Gln
                725                 730                 735

Tyr Ser Ile Pro Ser Ser Tyr His Lys Leu Lys Ser Leu Met Ala Arg
            740                 745                 750

Arg Thr Tyr Leu Glu Trp Pro Lys Glu Lys Ser Lys Arg Gly Leu Phe
        755                 760                 765

Trp Ala Asn Leu Arg Ala Ala Ile Asn Ile Lys Leu Thr Glu Gln Ala
770                 775                 780

Lys Lys
785

<210> SEQ ID NO 14
<211> LENGTH: 2355
<212> TYPE: DNA
<213> ORGANISM: Homo sapiens
<220> FEATURE:
<221> NAME/KEY: CDS
<222> LOCATION: (1)..(2355)

<400> SEQUENCE: 14 atg cca cat act ttg tgg atg gtg tgg gtc ttg ggg gtc atc atc agc      48
Met Pro His Thr Leu Trp Met Val Trp Val Leu Gly Val Ile Ile Ser
1               5                   10                  15 ctc tcc aag gaa gaa tcc tcc aat cag gct tct ctg tct tgt gac cgc      96
Leu Ser Lys Glu Glu Ser Ser Asn Gln Ala Ser Leu Ser Cys Asp Arg
            20                  25                  30 aat ggt atc tgc aag ggc agc tca gga tct tta aac tcc att ccc tca     144
Asn Gly Ile Cys Lys Gly Ser Ser Gly Ser Leu Asn Ser Ile Pro Ser
        35                  40                  45 ggg ctc aca gaa gct gta aaa agc ctt gac ctg tcc aac aac agg atc     192
Gly Leu Thr Glu Ala Val Lys Ser Leu Asp Leu Ser Asn Asn Arg Ile
```

|   |   |   |   |   |   |   |   |   |   |   |   |   |   |   |   |   |
|---|---|---|---|---|---|---|---|---|---|---|---|---|---|---|---|---|
| | | 50 | | | | 55 | | | | 60 | | | | | | |
| acc | tac | att | agc | aac | agt | gac | cta | cag | agg | tgt | gtg | aac | ctc | cag | gct | 240 |
| Thr | Tyr | Ile | Ser | Asn | Ser | Asp | Leu | Gln | Arg | Cys | Val | Asn | Leu | Gln | Ala | |
| 65 | | | | 70 | | | | 75 | | | | 80 | | | | |
| ctg | gtg | ctg | aca | tcc | aat | gga | att | aac | aca | ata | gag | gaa | gat | tct | ttt | 288 |
| Leu | Val | Leu | Thr | Ser | Asn | Gly | Ile | Asn | Thr | Ile | Glu | Glu | Asp | Ser | Phe | |
| | | | | 85 | | | | | 90 | | | | | 95 | | |
| tct | tcc | ctg | ggc | agt | ctt | gaa | cat | tta | gac | tta | tcc | tat | aat | tac | tta | 336 |
| Ser | Ser | Leu | Gly | Ser | Leu | Glu | His | Leu | Asp | Leu | Ser | Tyr | Asn | Tyr | Leu | |
| | | | 100 | | | | | 105 | | | | | 110 | | | |
| tct | aat | tta | tcg | tct | tcc | tgg | ttc | aag | ccc | ctt | tct | tct | tta | aca | ttc | 384 |
| Ser | Asn | Leu | Ser | Ser | Ser | Trp | Phe | Lys | Pro | Leu | Ser | Ser | Leu | Thr | Phe | |
| | | | 115 | | | | | 120 | | | | | 125 | | | |
| tta | aac | tta | ctg | gga | aat | cct | tac | aaa | acc | cta | ggg | gaa | aca | tct | ctt | 432 |
| Leu | Asn | Leu | Leu | Gly | Asn | Pro | Tyr | Lys | Thr | Leu | Gly | Glu | Thr | Ser | Leu | |
| | | | 130 | | | | | 135 | | | | | 140 | | | |
| ttt | tct | cat | ctc | aca | aaa | ttg | caa | atc | ctg | aga | gtg | gga | aat | atg | gac | 480 |
| Phe | Ser | His | Leu | Thr | Lys | Leu | Gln | Ile | Leu | Arg | Val | Gly | Asn | Met | Asp | |
| 145 | | | | | 150 | | | | | 155 | | | | | 160 | |
| acc | ttc | act | aag | att | caa | aga | aaa | gat | ttt | gct | gga | ctt | acc | ttc | ctt | 528 |
| Thr | Phe | Thr | Lys | Ile | Gln | Arg | Lys | Asp | Phe | Ala | Gly | Leu | Thr | Phe | Leu | |
| | | | | 165 | | | | | 170 | | | | | 175 | | |
| gag | gaa | ctt | gag | att | gat | gct | tca | gat | cta | cag | agc | tat | gag | cca | aaa | 576 |
| Glu | Glu | Leu | Glu | Ile | Asp | Ala | Ser | Asp | Leu | Gln | Ser | Tyr | Glu | Pro | Lys | |
| | | | 180 | | | | | 185 | | | | | 190 | | | |
| agt | ttg | aag | tca | att | cag | aac | gta | agt | cat | ctg | atc | ctt | cat | atg | aag | 624 |
| Ser | Leu | Lys | Ser | Ile | Gln | Asn | Val | Ser | His | Leu | Ile | Leu | His | Met | Lys | |
| | | | 195 | | | | | 200 | | | | | 205 | | | |
| cag | cat | att | tta | ctg | ctg | gag | att | ttt | gta | gat | gtt | aca | agt | tcc | gtg | 672 |
| Gln | His | Ile | Leu | Leu | Leu | Glu | Ile | Phe | Val | Asp | Val | Thr | Ser | Ser | Val | |
| | | | 210 | | | | | 215 | | | | | 220 | | | |
| gaa | tgt | ttg | gaa | ctg | cga | gat | act | gat | ttg | gac | act | ttc | cat | ttt | tca | 720 |
| Glu | Cys | Leu | Glu | Leu | Arg | Asp | Thr | Asp | Leu | Asp | Thr | Phe | His | Phe | Ser | |
| 225 | | | | | 230 | | | | | 235 | | | | | 240 | |
| gaa | cta | tcc | act | ggt | gaa | aca | aat | tca | ttg | att | aaa | aag | ttt | aca | ttt | 768 |
| Glu | Leu | Ser | Thr | Gly | Glu | Thr | Asn | Ser | Leu | Ile | Lys | Lys | Phe | Thr | Phe | |
| | | | | 245 | | | | | 250 | | | | | 255 | | |
| aga | aat | gtg | aaa | atc | acc | gat | gaa | agt | ttg | ttt | cag | gtt | atg | aaa | ctt | 816 |
| Arg | Asn | Val | Lys | Ile | Thr | Asp | Glu | Ser | Leu | Phe | Gln | Val | Met | Lys | Leu | |
| | | | 260 | | | | | 265 | | | | | 270 | | | |
| ttg | aat | cag | att | tct | gga | ttg | tta | gaa | tta | gag | ttt | gat | gac | tgt | acc | 864 |
| Leu | Asn | Gln | Ile | Ser | Gly | Leu | Leu | Glu | Leu | Glu | Phe | Asp | Asp | Cys | Thr | |
| | | | 275 | | | | | 280 | | | | | 285 | | | |
| ctt | aat | gga | gtt | ggt | aat | ttt | aga | gca | tct | gat | aat | gac | aga | gtt | ata | 912 |
| Leu | Asn | Gly | Val | Gly | Asn | Phe | Arg | Ala | Ser | Asp | Asn | Asp | Arg | Val | Ile | |
| | | | 290 | | | | | 295 | | | | | 300 | | | |
| gat | cca | ggt | aaa | gtg | gaa | acg | tta | aca | atc | cgg | agg | ctg | cat | att | cca | 960 |
| Asp | Pro | Gly | Lys | Val | Glu | Thr | Leu | Thr | Ile | Arg | Arg | Leu | His | Ile | Pro | |
| 305 | | | | | 310 | | | | | 315 | | | | | 320 | |
| agg | ttt | tac | tta | ttt | tat | gat | ctg | agc | act | tta | tat | tca | ctt | aca | gaa | 1008 |
| Arg | Phe | Tyr | Leu | Phe | Tyr | Asp | Leu | Ser | Thr | Leu | Tyr | Ser | Leu | Thr | Glu | |
| | | | | 325 | | | | | 330 | | | | | 335 | | |
| aga | gtt | aaa | aga | atc | aca | gta | gaa | aac | agt | aaa | gtt | ttt | ctg | gtt | cct | 1056 |
| Arg | Val | Lys | Arg | Ile | Thr | Val | Glu | Asn | Ser | Lys | Val | Phe | Leu | Val | Pro | |
| | | | 340 | | | | | 345 | | | | | 350 | | | |
| tgt | tta | ctt | tca | caa | cat | tta | aaa | tca | tta | gaa | tac | ttg | gat | ctc | agt | 1104 |
| Cys | Leu | Leu | Ser | Gln | His | Leu | Lys | Ser | Leu | Glu | Tyr | Leu | Asp | Leu | Ser | |
| | | | 355 | | | | | 360 | | | | | 365 | | | |
| gaa | aat | ttg | atg | gtt | gaa | gaa | tac | ttg | aaa | aat | tca | gcc | tgt | gag | gat | 1152 |
| Glu | Asn | Leu | Met | Val | Glu | Glu | Tyr | Leu | Lys | Asn | Ser | Ala | Cys | Glu | Asp | |

```
                   370                 375                 380
gcc tgg ccc tct cta caa act tta att tta agg caa aat cat ttg gca    1200
Ala Trp Pro Ser Leu Gln Thr Leu Ile Leu Arg Gln Asn His Leu Ala
385                 390                 395                 400 tca ttg gaa aaa acc gga gag act ttg ctc act ctg aaa aac ttg act    1248
Ser Leu Glu Lys Thr Gly Glu Thr Leu Leu Thr Leu Lys Asn Leu Thr
            405                 410                 415 aac att gat atc agt aag aat agt ttt cat tct atg cct gaa act tgt    1296
Asn Ile Asp Ile Ser Lys Asn Ser Phe His Ser Met Pro Glu Thr Cys
                420                 425                 430 cag tgg cca gaa aag atg aaa tat ttg aac tta tcc agc aca cga ata    1344
Gln Trp Pro Glu Lys Met Lys Tyr Leu Asn Leu Ser Ser Thr Arg Ile
        435                 440                 445 cac agt gta aca ggc tgc att ccc aag aca ctg gaa att tta gat gtt    1392
His Ser Val Thr Gly Cys Ile Pro Lys Thr Leu Glu Ile Leu Asp Val
    450                 455                 460 agc aac aac aat ctc aat tta ttt tct ttg aat ttg ccg caa ctc aaa    1440
Ser Asn Asn Asn Leu Asn Leu Phe Ser Leu Asn Leu Pro Gln Leu Lys
465                 470                 475                 480 gaa ctt tat att tcc aga aat aag ttg atg act cta cca gat gcc tcc    1488
Glu Leu Tyr Ile Ser Arg Asn Lys Leu Met Thr Leu Pro Asp Ala Ser
            485                 490                 495 ctc tta ccc atg tta cta gta ttg aaa atc agt agg aat gca ata act    1536
Leu Leu Pro Met Leu Leu Val Leu Lys Ile Ser Arg Asn Ala Ile Thr
                500                 505                 510 acg ttt tct aag gag caa ctt gac tca ttt cac aca ctg aag act ttg    1584
Thr Phe Ser Lys Glu Gln Leu Asp Ser Phe His Thr Leu Lys Thr Leu
        515                 520                 525 gaa gct ggt ggc aat aac ttc att tgc tcc tgt gaa ttc ctc tcc ttc    1632
Glu Ala Gly Gly Asn Asn Phe Ile Cys Ser Cys Glu Phe Leu Ser Phe
    530                 535                 540 act cag gag cag caa gca ctg gcc aaa gtc ttg att gat tgg cca gca    1680
Thr Gln Glu Gln Gln Ala Leu Ala Lys Val Leu Ile Asp Trp Pro Ala
545                 550                 555                 560 aat tac ctg tgt gac tct cca tcc cat gtg cgt ggc cag cag gtt cag    1728
Asn Tyr Leu Cys Asp Ser Pro Ser His Val Arg Gly Gln Gln Val Gln
            565                 570                 575 gat gtc cgc ctc tcg gtg tcg gaa tgt cac agg aca gca ctg gtg tct    1776
Asp Val Arg Leu Ser Val Ser Glu Cys His Arg Thr Ala Leu Val Ser
                580                 585                 590 ggc atg tgc tgt gct ctg ttc ctg ctg atc ctg ctc acg ggg gtc ctg    1824
Gly Met Cys Cys Ala Leu Phe Leu Leu Ile Leu Leu Thr Gly Val Leu
        595                 600                 605 tgc cac cgt ttc cat ggc ctg tgg tat atg aaa atg atg tgg gcc tgg    1872
Cys His Arg Phe His Gly Leu Trp Tyr Met Lys Met Met Trp Ala Trp
    610                 615                 620 ctc cag gcc aaa agg aag ccc agg aaa gct ccc agc agg aac atc tgc    1920
Leu Gln Ala Lys Arg Lys Pro Arg Lys Ala Pro Ser Arg Asn Ile Cys
625                 630                 635                 640 tat gat gca ttt gtt tct tac agt gag cgg gat gcc tac tgg gtg gag    1968
Tyr Asp Ala Phe Val Ser Tyr Ser Glu Arg Asp Ala Tyr Trp Val Glu
            645                 650                 655 aac ctt atg gtc cag gag ctg gag aac ttc aat ccc ccc ttc aag ttg    2016
Asn Leu Met Val Gln Glu Leu Glu Asn Phe Asn Pro Pro Phe Lys Leu
                660                 665                 670 tgt ctt cat aag cgg gac ttc att cct ggc aag tgg atc att gac aat    2064
Cys Leu His Lys Arg Asp Phe Ile Pro Gly Lys Trp Ile Ile Asp Asn
        675                 680                 685 atc att gac tcc att gaa aag agc cac aaa act gtc ttt gtg ctt tct    2112
Ile Ile Asp Ser Ile Glu Lys Ser His Lys Thr Val Phe Val Leu Ser
```

```
                    690                    695                    700
gaa aac ttt gtg aag agt gag tgg tgc aag tat gaa ctg gac ttc tcc      2160
Glu Asn Phe Val Lys Ser Glu Trp Cys Lys Tyr Glu Leu Asp Phe Ser
705                 710                 715                 720 cat ttc cgt ctt ttt gaa gag aac aat gat gct gcc att ctc att ctt      2208
His Phe Arg Leu Phe Glu Glu Asn Asn Asp Ala Ala Ile Leu Ile Leu
                725                 730                 735 ctg gag ccc att gag aaa aaa gcc att ccc cag cgc ttc tgc aag ctg      2256
Leu Glu Pro Ile Glu Lys Lys Ala Ile Pro Gln Arg Phe Cys Lys Leu
            740                 745                 750 cgg aag ata atg aac acc aag acc tac ctg gag tgg ccc atg gac gag      2304
Arg Lys Ile Met Asn Thr Lys Thr Tyr Leu Glu Trp Pro Met Asp Glu
        755                 760                 765 gct cag cgg gaa gga ttt tgg gta aat ctg aga gct gcg ata aag tcc      2352
Ala Gln Arg Glu Gly Phe Trp Val Asn Leu Arg Ala Ala Ile Lys Ser
770                 775                 780 tag                                                                   2355

<210> SEQ ID NO 15
<211> LENGTH: 784
<212> TYPE: PRT
<213> ORGANISM: Homo sapiens

<400> SEQUENCE: 15

Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
    130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255
```

-continued

```
Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
            275                 280                 285

Leu Asn Gly Val Gly Asn Phe Arg Ala Ser Asp Asn Asp Arg Val Ile
            290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
                340                 345                 350

Cys Leu Leu Ser Gln His Leu Lys Ser Leu Glu Tyr Leu Asp Leu Ser
            355                 360                 365

Glu Asn Leu Met Val Glu Tyr Leu Lys Asn Ser Ala Cys Glu Asp
            370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
            435                 440                 445

His Ser Val Thr Gly Cys Ile Pro Lys Thr Leu Glu Ile Leu Asp Val
            450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
            515                 520                 525

Glu Ala Gly Gly Asn Asn Phe Ile Cys Ser Cys Glu Phe Leu Ser Phe
            530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
            580                 585                 590

Gly Met Cys Cys Ala Leu Phe Leu Leu Ile Leu Leu Thr Gly Val Leu
            595                 600                 605

Cys His Arg Phe His Gly Leu Trp Tyr Met Lys Met Met Trp Ala Trp
            610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
                645                 650                 655

Asn Leu Met Val Gln Glu Leu Glu Asn Phe Asn Pro Pro Phe Lys Leu
            660                 665                 670

Cys Leu His Lys Arg Asp Phe Ile Pro Gly Lys Trp Ile Ile Asp Asn
            675                 680                 685
```

```
Ile Ile Asp Ser Ile Glu Lys Ser His Lys Thr Val Phe Val Leu Ser
        690                 695                 700
Glu Asn Phe Val Lys Ser Glu Trp Cys Lys Tyr Glu Leu Asp Phe Ser
705                 710                 715                 720
His Phe Arg Leu Phe Glu Glu Asn Asn Asp Ala Ala Ile Leu Ile Leu
                725                 730                 735
Leu Glu Pro Ile Glu Lys Lys Ala Ile Pro Gln Arg Phe Cys Lys Leu
            740                 745                 750
Arg Lys Ile Met Asn Thr Lys Thr Tyr Leu Glu Trp Pro Met Asp Glu
        755                 760                 765
Ala Gln Arg Glu Gly Phe Trp Val Asn Leu Arg Ala Ala Ile Lys Ser
    770                 775                 780

<210> SEQ ID NO 16
<211> LENGTH: 399
<212> TYPE: DNA
<213> ORGANISM: Homo sapiens
<220> FEATURE:
<221> NAME/KEY: CDS
<222> LOCATION: (1)..(399)

<400> SEQUENCE: 16 atg acg ggg gaa ctt gag gtt aag aac atg gac atg aag ccg ggg tca      48
Met Thr Gly Glu Leu Glu Val Lys Asn Met Asp Met Lys Pro Gly Ser
1               5                   10                  15 acc ctg aag atc aca ggc agc atc gcc gat ggc act gat ggc ttt gta      96
Thr Leu Lys Ile Thr Gly Ser Ile Ala Asp Gly Thr Asp Gly Phe Val
                20                  25                  30 att aat ctg ggc cag ggg aca gac aag ctg aac ctg cat ttc aac cct     144
Ile Asn Leu Gly Gln Gly Thr Asp Lys Leu Asn Leu His Phe Asn Pro
            35                  40                  45 cgc ttc agc gaa tcc acc att gtc tgc aac tca ttg gac ggc agc aac     192
Arg Phe Ser Glu Ser Thr Ile Val Cys Asn Ser Leu Asp Gly Ser Asn
        50                  55                  60 tgg ggg caa gaa caa cgg gaa gat cac ctg tgc ttc agc cca ggg tca     240
Trp Gly Gln Glu Gln Arg Glu Asp His Leu Cys Phe Ser Pro Gly Ser
65                  70                  75                  80 gag gtc aag ttc aca gtg acc ttt gag agt gac aaa ttc aag gtg aag     288
Glu Val Lys Phe Thr Val Thr Phe Glu Ser Asp Lys Phe Lys Val Lys
                85                  90                  95 ctg cca gat ggg cac gag ctg act ttt ccc aac agg ctg ggt cac agc     336
Leu Pro Asp Gly His Glu Leu Thr Phe Pro Asn Arg Leu Gly His Ser
            100                 105                 110 cac ctg agc tac ctg agc gta agg ggc ggg ttc aac atg tcc tct ttc     384
His Leu Ser Tyr Leu Ser Val Arg Gly Gly Phe Asn Met Ser Ser Phe
        115                 120                 125 aag tta aaa gaa taa                                                 399
Lys Leu Lys Glu
    130

<210> SEQ ID NO 17
<211> LENGTH: 132
<212> TYPE: PRT
<213> ORGANISM: Homo sapiens

<400> SEQUENCE: 17

Met Thr Gly Glu Leu Glu Val Lys Asn Met Asp Met Lys Pro Gly Ser
1               5                   10                  15

Thr Leu Lys Ile Thr Gly Ser Ile Ala Asp Gly Thr Asp Gly Phe Val
                20                  25                  30
```

```
Ile Asn Leu Gly Gln Gly Thr Asp Lys Leu Asn Leu His Phe Asn Pro
        35                  40                  45

Arg Phe Ser Glu Ser Thr Ile Val Cys Asn Ser Leu Asp Gly Ser Asn
 50                  55                  60

Trp Gly Gln Glu Gln Arg Glu Asp His Leu Cys Phe Ser Pro Gly Ser
 65                  70                  75                  80

Glu Val Lys Phe Thr Val Thr Phe Glu Ser Asp Lys Phe Lys Val Lys
                 85                  90                  95

Leu Pro Asp Gly His Glu Leu Thr Phe Pro Asn Arg Leu Gly His Ser
            100                 105                 110

His Leu Ser Tyr Leu Ser Val Arg Gly Gly Phe Asn Met Ser Ser Phe
        115                 120                 125

Lys Leu Lys Glu
    130
```

```
<210> SEQ ID NO 18
<211> LENGTH: 29
<212> TYPE: DNA
<213> ORGANISM: Artificial sequence
<220> FEATURE:
<223> OTHER INFORMATION: primer

<400> SEQUENCE: 18
atcgaattct gacggggaa cttgaggtt                                        29

<210> SEQ ID NO 19
<211> LENGTH: 30
<212> TYPE: DNA
<213> ORGANISM: Artificial sequence
<220> FEATURE:
<223> OTHER INFORMATION: primer

<400> SEQUENCE: 19
atcctcgagt tattctttta acttgaaaga                                      30

<210> SEQ ID NO 20
<211> LENGTH: 558
<212> TYPE: DNA
<213> ORGANISM: Homo sapiens

<400> SEQUENCE: 20
cccccccagc tctagggacg accacacccc cacccagttc tgcctgtctc tctctgcgcc     60
tttgactctg ttgggtgggg acaaggctcc cgggcctgca ccctcccgca gctctcagca    120
tccctatttg tccaagtgca cccctgaccc tggacttccg agtgcttctg ccctgcagca    180
gcccccacct ctatccttgg ggtttgagct ttgctgtttc agtcaggcag ccccaggag     240 ctgcaagggg agtgtgggtg cttctcttag tccaggccca gctcccctat cctggcctga    300
ctgttgcagg gctcggggtg tgggcacagg ctgctggcag gaggcaggga gccatctcct    360
gatgcttggt gttagaygtg tgtgtgcgca gggcacacgt ctgtgagtgt ctgtgtggcg    420
ggcacacctg tcttctgttt cttgtttgag ccccttttgg actgtcctca ctggataacc    480
tcatctccca gagataatgg tctttgtcag tgagagactg attttttttt tttttttttt    540 tttttgaga cggagtct                                                   558

<210> SEQ ID NO 21
<211> LENGTH: 28
<212> TYPE: DNA
<213> ORGANISM: Artificial sequence
<220> FEATURE:
<223> OTHER INFORMATION: primer
```

```
<400> SEQUENCE: 21
atcgaattcg ggcctgtggt atatgaaa                                              28

<210> SEQ ID NO 22
<211> LENGTH: 30
<212> TYPE: DNA
<213> ORGANISM: Artificial sequence
<220> FEATURE:
<223> OTHER INFORMATION: primer

<400> SEQUENCE: 22
atcggtaccc taggacttta tcgcagctct                                            30
```

METHOD OF EXAMINING INFLAMMATORY DISEASE AND METHOD OF SCREENING REMEDY FOR IMFLAMMATORY DISEASE

This application is the U. S. National Stage under 35 USC §371 of International Application PCT/JP2006/300224 filed Jan. 11, 2006, which claims priority under 35 USC §119 (a)-(d) of Application No. 2005-004297 filed in Japan on Jan. 11, 2005.

TECHNICAL FIELD

The present invention relates to a method of diagnosing an inflammatory disease such as myocardial infarction, and a method of screening a remedy for an inflammatory disease.

BACKGROUND ART

In recent years, risks of death in coronary diseases such as myocardial infarction have increased with changes in life styles (Non-patent Document 1 or 2). Therefore, a method of diagnosing a critical risk for any of those diseases at an early stage has been expected to be developed.

The possibilities of development of coronary diseases such as myocardial infarction due to genetic predispositions have been suggested in the art. Several methods of diagnosing myocardial infarction on the basis of the presence or absence of a gene mutation have been known in the art. For instance, a method of diagnosing a risk of the onset of myocardial infarction by analyzing the polymorphism of a prostacyclin synthase gene has been known (Patent Document 1). However, for diagnosing more precisely, another method for the diagnosis has been expected to be developed.

A Toll-like receptor is a single-spanning membrane receptor. It is isolated as a homologue of Toll, one of receptors of insects, and is responsible for an immune response or the like (Non-patent Document 3). Polymorphisms in several portions of a gene that encodes the Toll-like receptor have been known to relate to asthma (Non-patent Document 4). However, there is no finding with respect to the relationship between the polymorphism of the Toll-like receptor gene and inflammatory diseases such as myocardial infarction.

Galectins are proteins having affinities for galactose. In mammals, at present, 10 different galectins are known. Among those, galectin-2 is known to form a noncovalent homodimer composed of a 14 KDa subunit and it is self-aggregated to lose its activity in the absence of a reducing agent. In addition, the details of physiological functions of galectin-2 have not been known even though in many cases the expression of galectin-2 is found in epithelial cells in normal adult human tissues, mainly in the lower part of the small intestine (Non-patent Document 5).

Patent Document 1: JP2002-136291
Non-patent Document 1: Nature Medicine, 1997, vol. 3, p 600-601
Non-patent Document 2: New England Journal of Medicine, 1997, vol. 337, p 1360-1369
Non-patent Document 3: J. Biol. Chem., Vol. 278, Issue 40, 38105-38108, 2003
Non-patent Document 4: Genes Immun. 2004 August; 5 (5): 343-6
Non-patent Document 5: Trends in Glycoscience and Glycotechnology, 1997, vol. 9, No. 45, p 87-93

DISCLOSURE OF THE INVENTION

An object of the present invention is to provide a method of precisely diagnosing a risk of the onset of an inflammatory disease such as myocardial infarction, or the presence or absence of the onset thereof. Another object of the present invention is to provide a method of screening a remedy for an inflammatory disease, such as myocardial infarction.

The inventors of the present invention have intensively studied for solving the above-mentioned problems. As a result, the inventors of the present invention have found that single nucleotide polymorphisms of a Toll-like receptor gene are associated with myocardial infarction. In addition, the inventors of the present invention have found that the Toll-like receptors show a specific interaction with galectin-2 and thus a remedy for an inflammatory disease, such as myocardial infarction, can be obtained by screening a substance capable of altering the interaction, thereby completed the present invention.

That is, the present invention provides the followings.

(1) A method of diagnosing an inflammatory disease, comprising:
analyzing a polymorphism of a Toll-like receptor gene, and
diagnosing an inflammatory disease based on a result of the analysis.

(2) The method according to (1), wherein the polymorphism is a single-nucleotide polymorphism.

(3) The method according to (2), wherein the Toll-like receptor gene is a Toll-like receptor 1 gene, and the single-nucleotide polymorphism present on the Toll-like receptor 1 gene is a polymorphism of a nucleotide corresponding to the nucleotide at position 201 of SEQ ID NO: 1 or of a nucleotide corresponding to the nucleotide at position 197 of SEQ ID NO: 2.

(4) The method according to (2), wherein the Toll-like receptor gene is a Toll-like receptor 4 gene, and the single-nucleotide polymorphism present on the Toll-like receptor 4 gene is a polymorphism of a nucleotide corresponding to the nucleotide at position 202 of SEQ ID NO: 3.

(5) The method according to (1), wherein the Toll-like receptor gene is a Toll-like receptor 1 gene, and the polymorphism of the Toll-like receptor 1 gene is a polymorphism which is in linkage disequilibrium with a single-nucleotide polymorphism of the nucleotide at position 201 of SEQ ID NO: 1 or the nucleotide at position 197 of SEQ ID NO: 2.

(6) The method according to (1), wherein the Toll-like receptor gene is a Toll-like receptor 4 gene, and the polymorphism of the Toll-like receptor 4 gene is a polymorphism which is in linkage disequilibrium with a single-nucleotide polymorphism of the nucleotide at position 202 of SEQ ID NO: 3.

(7) The method according to any one of (1) to (6), wherein the inflammatory disease is myocardial infarction.

(8) A probe for diagnosing an inflammatory disease, which comprises a sequence of 10 or more nucleotides in SEQ ID NO: 1 including the nucleotide at position 201, or a complementary sequence thereof.

(9) A primer for diagnosing an inflammatory disease, which is capable of amplifying a region comprising the nucleotide at position 201 of SEQ ID NO: 1.

(10) A probe for diagnosing an inflammatory disease, which comprises a sequence of 10 or more nucleotides in SEQ ID NO: 2 including the nucleotide at position 197, or a complementary sequence thereof.

(11) A primer for diagnosing an inflammatory disease, which is capable of amplifying a region comprising the nucleotide at position 197 of SEQ ID NO: 2.

(12) A probe for diagnosing an inflammatory disease, which comprises a sequence of 10 or more nucleotides in SEQ ID NO: 3 including the nucleotide at position 202, or a complementary sequence thereof.

(13) A primer for diagnosing an inflammatory disease, which is capable of amplifying a region comprising the nucleotide at position 202 of SEQ ID NO: 3.

(14) A method of screening a remedy for an inflammatory disease, comprising the steps of:

adding a pharmaceutical candidate substance into a screening system comprising a Toll-like receptor and a galectin-2;

measuring an interaction between the Toll-like receptor and the galectin-2; and selecting a substance that alters the interaction.

(15) The method according to (14), wherein the Toll-like receptor is a Toll-like receptor 1 or a Toll-like receptor 2.

DESCRIPTION OF THE PREFERRED EMBODIMENTS

Figure 1:
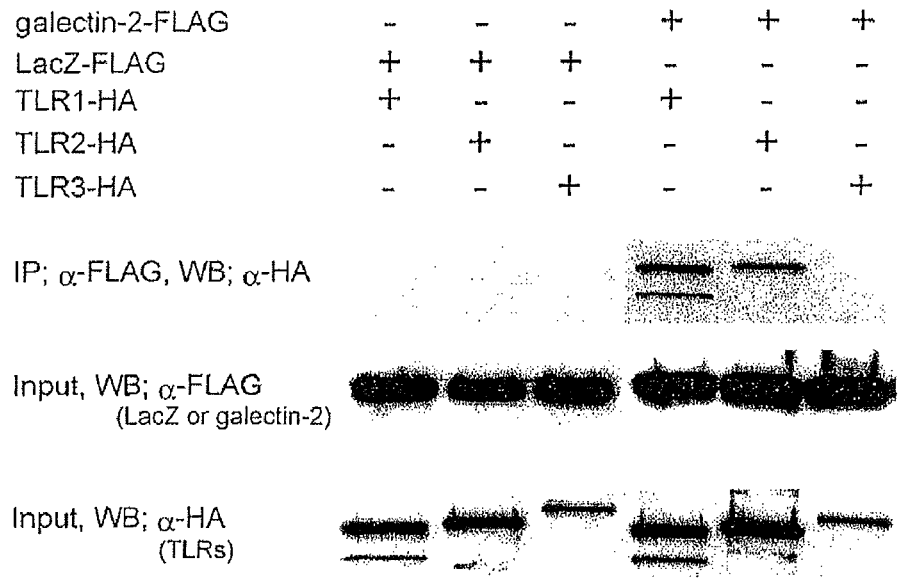
FIG. 1 is a diagram representing the results of an analysis of the interaction between TLR and galectin-2 by immunoprecipitation. IP means immunoprecipitation and WB means Western blot.
Figure 2:
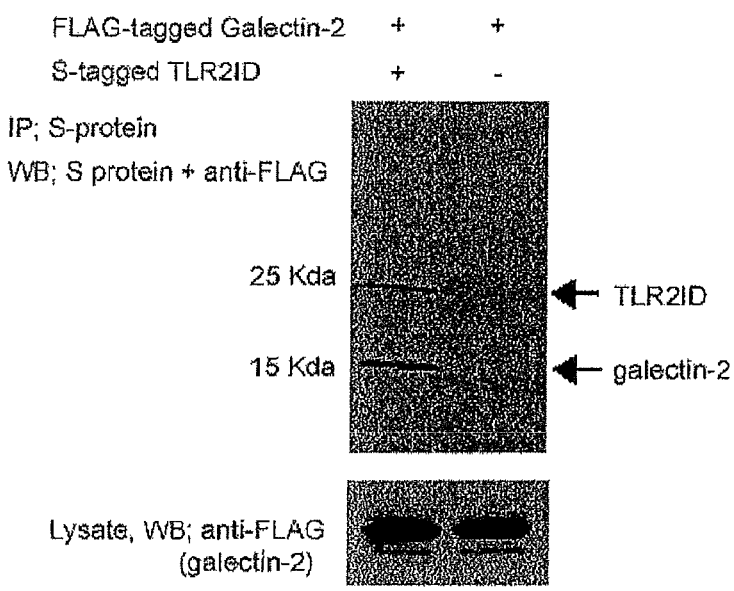
FIG. 2 is a diagram representing the results of an analysis of the interaction between an intracellular domain of TLR2 and galectin-2 by immunoprecipitation. IP means immunoprecipitation and WB means Western blot.

<1> Diagnosis Method of the Present Invention

The method of the present invention comprises analyzing a genetic polymorphism associated with an inflammatory disease of a Toll-like receptor (TLR) gene, and diagnosing the inflammatory disease based on the analysis. The inflammatory disease is not particularly limited as long as it is one of diseases where the induction of cell adhesion factors and cytokines involved in inflammation is observed, and examples thereof include chronic rheumatism systemic erythematosus, inflammatory enterocolitis, various kinds of allergosis, bacterial shock, and coronary artery diseases such as myocardial infarction and stroke, and particularly include myocardial infarction. In the present invention, the term "diagnosis" includes diagnosis for a risk of the onset of an inflammatory disease and diagnosis for the presence or absence of the onset.

As the Toll-like receptor gene, Toll-like receptor 1 (TLR1) gene or Toll-like receptor 4 (TLR4) gene is preferable. As the TLR1 gene, a human TLR1 gene is preferable. For example, it may be a gene comprising a sequence registered as Accession No. U88540 in the database of the National Center for Biotechnology Information (NCBI). As the TLR4 gene, a human TLR 4 gene is preferable. For example, it may be a gene comprising a sequence registered as Accession No. AF172169 in the database of the National Center for Biotechnology Information (NCBI). In addition, TLR1 gene and TLR4 gene are not limited to the genes comprising the above-mentioned sequences because there are racial differences and so on in these genes and substitutions, deletions, or the like may occur in nucleotides other than those associated with inflammatory diseases.

In addition, the sequence of the Toll-like receptor gene may be analyzed with respect to either of its sense strand or antisense strand.

There is no particular limitation on the kinds of genetic polymorphisms as long as they are associated with inflammatory diseases, and single nucleotide polymorphism (polymorphisms) (SNPs), variable number of tandem repeat (VNTR) are included.

Single nucleotide polymorphisms of the TLR1 gene associated with inflammatory disease are not particularly limited, and examples thereof include a polymorphism at nucleotide 1805 (nucleotide at position 197 of SEQ ID NO: 2).

A sequence containing the nucleotide "1805" may be, for example, the sequence of SEQ ID NO: 1. The nucleotide "1805" corresponds to the nucleotide at position 201 of this sequence. In the TLR1 gene on the human chromosome, there is a polymorphism of thymine (T) and guanine (G) at this nucleotide.

A sequence containing the nucleotide "130" may be, for example, the sequence of SEQ ID NO: 2. The nucleotide "130" corresponds to the nucleotide at position 197 of this sequence. In the TLR1 gene on the human chromosome, there is a polymorphism of thymine (T) and cytosine (C) at the nucleotide.

The phrase "correspond to" means a corresponding nucleotide in a region containing the above-mentioned sequence on the human TLR1 gene. Even if the above-mentioned sequence is slightly modified at a position other than the SNP depending on a racial difference or the like, an analysis of the corresponding nucleotide therein may also be included.

Single nucleotide polymorphisms of the TLR4 gene associated with inflammatory disease include, but not limited to, a polymorphism at nucleotide "−1440" (nucleotide at position 202 of SEQ ID NO: 3). The number "−1440" is the number according to Dunnen J. T. and Antonarakis S. E. Hum. Mutation 15, 7-12, 2000. A sequence containing the nucleotide "−1440" may be, for example, the sequence of SEQ ID NO: 3. The nucleotide "−1440" corresponds to the nucleotide at position 202 of this sequence. In the TLR4 gene on the human chromosome, there is a polymorphism of thymine (T) and cytosine (C) at this nucleotide.

The phrase "correspond to" means a corresponding nucleotide in a region containing the above-mentioned sequence on the human TLR4 gene. Even if the above-mentioned sequence is slightly modified at a position other than the SNP depending on a racial difference or the like, an analysis of the corresponding nucleotide therein may also be included.

The inflammatory disease can be diagnosed by analyzing the above-mentioned nucleotide polymorphisms singly or in combination. In addition, the diagnosis may be carried out with respect to a polymorphism which is in linkage disequilibrium with the above-mentioned single nucleotide polymorphisms. Polymorphisms which are in linkage disequilibrium include single nucleotide polymorphisms of other nucleotides and VNTRs.

Samples to be used in analysis of genetic polymorphisms of TLR genes include, but not limited to, body fluid such as urine and blood, cells such as mucous cells, and body hair such as scalp hair. For the analysis of genetic polymorphisms, these samples may be directly used, but preferably chromosomal DNA is isolated from these samples by ordinary methods and then used for the analysis.

The analysis of genetic polymorphisms of TLR genes can be performed by conventional techniques for analyzing the genetic polymorphisms. Examples of the analysis include, but not limited to, sequence analysis, PCR, and hybridization.

The sequencing can be performed by conventional procedures. Specifically, a sequencing reaction is performed using a primer located several tens of nucleotides 5' side from a polymorphic site. From the result of such an analysis, the kind of the nucleotide on the corresponding position can be determined. Preferably, when the sequencing is carried out, a fragment containing a polymorphic nucleotide is amplified by PCR or the like.

Further, the analysis can be carried out by detecting the presence of an amplified product in PCR. For instance, primers having a sequence corresponding to a region containing a polymorphic site and corresponding to the respective polymorphic nucleotides are prepared and then used in PCR, followed by detecting the presence of an amplified product to determine the kind of the polymorphic nucleotide.

Alternatively, the presence of an amplified product may be determined using a LAMP method (JP 3313358 B), a nucleic acid sequence-based amplification method (NASBA method; JP 2843586 B), and an ICAN method (JP 2002-233379 A). Any of other methods, such as a single-chain amplification method, may also be employed.

Further, a DNA fragment containing the polymorphic site may be amplified and the amplified product may be then electrophoresed, followed by determining the kind of the nucleotide based on a difference in mobility. An example of such a method includes single-strand conformation polymorphism (PCR-SSCP) (Genomics. 1992 Jan. 1; 12 (1): 139-146). Specifically, at first, a DNA containing a polymorphic site of the TLR gene is amplified and the amplified DNA is then dissociated to single stranded DNAs. Subsequently, the dissociated single stranded DNAs are separated on a non-denaturing gel and the kind of the nucleotide can be then determined based on a difference in mobilities of the dissociated single stranded DNAs on the gel.

Further, when a polymorphic nucleotide is included in a restriction-enzyme recognition sequence, the analysis may depend on the presence or absence of digestion with a restriction enzyme (RFLP method). In this case, at first, a DNA sample is digested with a restriction enzyme. The DNA fragment is then separated, thereby allowing the determination of the kind of the nucleotide based on the size of the detected DNA fragment. Regarding the polymorphism of nucleotide "1805" of the TLR1 gene, a PstI recognition site occurs in a case where the polymorphic nucleotide is G, so the polymorphism can be detected by the presence or absence of PstI digestion.

Based on the polymorphism analyzed by the method as described above, a diagnosis of inflammatory disease is carried out.

For instance, in the case of carrying out the diagnosis on the basis of the nucleotide "1805" of the TLR1 gene, when the nucleotide is q it is diagnosed that a risk of the onset of inflammatory disease is high, or a possibility of suffering from inflammatory disease is high. In addition, diagnosis may be performed by considering a polymorphism of an allelic gene. For example, when the genotype is GG or TG allele, it can be diagnosed that a risk of the onset of inflammatory disease is higher, or a possibility of suffering from inflammatory disease is higher, as compared with TT allele.

In the case of carrying out the diagnosis on the basis of the polymorphism of the nucleotide "130" of the TLR1 gene, when the nucleotide is C, it can be diagnosed that a risk of the onset of inflammatory disease is high, or a possibility of suffering from inflammatory disease is high. Further, diagnosis may be performed by considering a polymorphism of an allelic gene. For example, when the genotype is CC or TC allele, it can be diagnosed that a risk of the onset of inflammatory disease is higher, or a possibility of suffering from inflammatory disease is higher, as compared with TT allele.

In the case of carrying out the diagnosis on the basis of the polymorphism of the nucleotide "−1440" of the TLR4 gene, when the nucleotide is C, it can be diagnosed that a risk of the onset of inflammatory disease is high, or a possibility of suffering from inflammatory disease is high. Further, diagnosis may be performed by considering a polymorphism of an allelic gene. For example, when the genotype is CC allele, it can be diagnosed that a risk of the onset of inflammatory disease is higher, or a possibility of suffering from inflammatory disease is higher, as compared with TC or TT allele.

In the diagnosis method of the present invention, in addition to the polymorphism of the TLR genes, polymorphisms of other genes may be analyzed to determine an inflammatory disease on the basis of a combination of polymorphisms of these genes. One of the other genes may be a galectin-2 gene. The sequence of the galectin-2 gene may be one registered as NT_011520 in NCBI. Polymorphisms of the galectin-2 gene include a polymorphism at nucleotide "3279" of intron 1. This nucleotide corresponds to the nucleotide at position 377 of SEQ ID NO: 20. In the human galectin-2 gene, a polymorphism of A and T is present. A risk of inflammatory disease is high in the case of TT as compared with a genotype AA (Nature, 2004 May 6; 429 (6987): 72-5).

Further, in the diagnosis method of the present invention, a diagnosis can also be carried out in combination with polymorphisms of the lymphotoxin a gene which has been known to associate with myocardial infarction ((Nat Genet. 2002 December; 32 (4): 650-4.2002; WO2004/015100).

<2> Diagnosis Agent of the Present Invention

In the present invention, diagnosis agents, such as primers and probes, for diagnosing inflammatory diseases are provided. Examples of the probes include: a probe comprising a sequence in SEQ ID NO: 1 including the nucleotide at position 201 or a complementary sequence thereof; a probe comprising a sequence in SEQ ID NO: 2 including the nucleotide at position 197 or a complementary sequence thereof; and a probe comprising a sequence in SEQ ID NO: 3 including the nucleotide at position 202 or a complementary sequence thereof.

Further, examples of the primers include: a primer capable of distinguishing a polymorphism of the nucleotide at position 201 of SEQ ID NO: 1, for example, a primer capable of amplifying a region comprising the nucleotide at position 201 of SEQ ID NO: 1; a primer capable of distinguishing a polymorphism of the nucleotide at position 197 of SEQ ID NO: 2, for example a primer capable of amplifying a region comprising the nucleotide at position 197 of SEQ ID NO: 2; and a primer capable of distinguishing a polymorphism of the nucleotide at position 202 of SEQ ID NO: 3, for example a primer capable of amplifying a region comprising the nucleotide at position 202 of SEQ ID NO: 3. Primers may be a primer set of a forward primer and a reverse primer designed on both sides of a region (preferably region having a length of 50 to 1,000 nucleotides) containing the polymorphic site. In addition, when used in a sequence analysis or a single chain amplification, an example of the primer may be one having a 5'-side region from the above-mentioned polymorphic nucleotides, preferably having a sequence of the region 30 to 100 nucleotide upstream from the polymorphic site, or one having a sequence complementary to 3'-side region from the above-mentioned polymorphic nucleotides, preferably having a sequence complementary to the region 30 to 100 nucleotide downstream from the polymorphic site. The primers to be used for determining the polymorphisms on the basis of the presence or absence of the amplification in PCR include a primer comprising a sequence including the above-mentioned polymorphic nucleotide on the 3'-side and a primer comprising a sequence complementary to the sequence including the above-mentioned polymorphic nucleotide and containing a nucleotide complementary to the polymorphic nucleotide on the 3'-side.

The length of such primers and probes is not particularly limited, for instance, oligonucleotides with a length of 10 to 100 nucleotides are preferable, and oligonucleotides with a length of 15 to 50 nucleotides are more preferable. In addition, the diagnosis agents of the present invention may further comprise PCR polymerase and buffer as well as these primers and probes.

The diagnosis agents of the present invention may further comprise primers and probes for analyzing polymorphisms of the galectin-2 gene. Such probes include a probe comprising a sequence of SEQ ID NO: 20 including the nucleotide at position 377 or a complementary sequence thereof, whereas such primers include a primer capable of amplifying a DNA comprising a sequence of SEQ ID NO: 20 including the nucleotide at position 377.

<3> Screening Method

The screening method of the present invention is a method for screening a remedy for an inflammatory disease, comprising the steps of: adding a pharmaceutical candidate substance to a screening system comprising a toll-like receptor (TLR) and galectin-2; measuring an interaction between the TLR and the galectin-2; and selecting a substance that alters the interaction.

For TLR and galectin-2 (Nature. 2004 May 6; 429 (6987): 72-5), polymorphisms on their respective genes are shown to be associated with inflammatory diseases, such as myocardial infarction, and these proteins specifically interact with each other in vivo. Thus, any substance capable of altering their interaction can be a pharmaceutical candidate substance to inflammatory diseases. The TLR protein is preferably TLR1 or TLR2.

The pharmaceutical candidate substance is not particularly limited, and may be a low-molecular synthetic compound or a compound derived from a natural source. Further, it may be a peptide. Individual test substances or a compound library comprising these substances may be used in screening. Among these candidate substances, a substance that alters the interaction between TLR and galectin-2 is selected as a therapeutic drug for inflammatory disease. Here, the meaning of the term "alter" includes inhibiting the interaction as well as strengthening the interaction.

The screening system comprising TLR and galectin-2 means a screening system comprising both of the proteins and it may be an in vitro system or a cell-based system. The screening system may be a system to which these proteins are directly added or a system where these proteins are to be present by translation of mRNAs transcribed from the corresponding genes.

Specific examples of the in vitro screening system include a pull-down assay using a TLR protein and a galectin-2 protein, and a detection method using surface plasmon resonance as described below.

The TLR protein and galectin-2 protein to be used in in vitro screening system may be recombinant proteins or naturally-occurring proteins. Further, they may be chemically synthesized. Origins of the proteins are not particularly limited, and any protein from eukaryotes including humans and other animals can be used, preferably, any protein of human origin can be used. An example of a TLR1 protein of human origin includes one comprising the amino acid sequence of SEQ ID NO: 13. An example of a TLR2 protein of human origin includes one comprising the amino acid sequence of SEQ ID NO: 15. Further, as long as it has an affinity with galectin-2, it may have an amino acid sequence of SEQ ID NO: 13 or 15 with one- or several-amino acid substitution, deletion, or addition.

On the other hand, an example of a galectin-2 protein of human origin includes one comprising the amino acid sequence of SEQ ID NO: 17. In addition, as long as it has an affinity with TLR2, it may have an amino acid sequence of SEQ ID NO: 17 with one- or several-amino acid substitution, deletion, or addition. The term "several" means preferably 2 to 50, more preferably 2 to 20, particularly preferably 2 to 10.

Further, a partial peptide of the protein having a interaction region may be used. The TLR is not always easily expressed because of its large molecular weight, so an intracellular domain involved in the interaction with galectin-2 may be used. Alternatively, a protein fused with another peptide may also be used. Peptides to be fused include peptide tags, such as GST, His-tag, and S-tag, which can be used in a pull-down assay and a purification.

For obtaining proteins by gene recombination, for example, DNAs having nucleotide sequences of SEQ ID NO: 12 (TLR1), SEQ ID NO: 14 (TLR2), and SEQ ID NO: 16 (galectin-2) are introduced into *E. coli* cells, animal cells, or the like to express the recombinant proteins, followed by purifying the proteins, respectively. Proteins do not always have to be purified, and a partially-purified product or a cell extract may be used in detection of the interaction. Vectors for introducing the above-mentioned DNAs into *E. coli* include pET vector (Novagen) and pGEX vector (Amersham Pharmacia). Vectors for introduction into animal cells include pcDNA vector (Invitrogen) and pcDNA (Invitrogen).

In the case of carrying out the pull-down assay as an in vitro system, TLR and galectin-2 proteins are incubated in vitro. The interaction between the proteins can be evaluated such that a complex is collected by using an antibody against one of these proteins or an antibody against the peptide tag to be fused or affinity column, followed by detecting the other protein to be bound to that protein. The screening can be carried out such that the test substances are added to the system and any substance that affects the interaction is then selected. In the pull-down assay, one protein may be labeled with a labeling material such as a radioisotope or biotin and then used for the detection.

Further, a system using a biosensor in which a surface plasmon resonance phenomenon is applied can also be exemplified as an in vitro screening system. The biosensor using the surface plasmon resonance phenomenon allows the interaction between the proteins to be observed as a surface plasmon resonance signal in real time with a small amount of protein samples without labeling (e.g., BIAcore, manufactured by Pharmacia). Therefore, the interaction between TLR and galectin-2 may be evaluated using the biosensor, such as BIAcore. Further, the screening of the present invention can be carried out by high through put screening with combinatorial chemistry (Science 1996, 273 p 458-64, Nature 1996, 384 p 11-13).

Further, as another screening system, a system for detection with fluorescence can be used (Fluorescence Resonance Energy Transfer (FRET)).

In addition, the screening can also be carried out in a cell-based system. For example, there may be employed a method using immunoprecipitation. That is, cells expressing TLR and galectin-2 are incubated and then collected, followed by recovering a complex by an antibody directed to one of the proteins. After that, the other one of the proteins is detected by an antibody directed to the protein. Thus, the interaction between the proteins can be detected and the effect of the test sample on the interaction can be evaluated. In this case, both of the proteins may be proteins endogenously expressed in cells, or one or both of them may be proteins exogenously expressed in cells. Examples of the cells to be used include, but not limited to, CHO cells and COS cells.

In the case of exogenously expressing the proteins in animal cells, for example, genes encoding TLR and/or galectin-2 as described above can be expressed by inserting them into vectors for expressing exogenous genes, such as pSV2neo, pcDNA I, and pCD8. In addition, these proteins may be expressed as fusion proteins with peptide tags, such as Myc tag and Flag tag.

The screening system using cells may also employ a two-hybrid method using yeast or animal cells.

In the yeast two-hybrid method, a vector that expresses a fusion protein obtained by fusing one of TLR and galectin-2 or a partial peptide thereof with a GAL4-DNA binding domain is constructed. In addition, a vector that expresses a fusion protein obtained by fusing the other one of the proteins or a partial peptide thereof with a transcription activation domain for VP16, or GAL4 is constructed. Then, these constructed vectors are introduced into yeast cells together with a vector comprising a reporter gene, followed by carrying out an assay of a compound using the reporter activity as an index in the presence of a sample containing a test substance. The interaction between TLR protein and galectin-2 protein induces the expression of a reporter gene. However, the expression of the reporter gene is suppressed when the interaction between the proteins is inhibited by a test compound. Examples of the reporter gene include, but not limited to, an Ade2 gene, a LacZ gene, a CAT gene, a luciferase gene, and a GFP gene, as well as an HIS3 gene. Besides the yeast, the screening by the two-hybrid method can also be carried out using mammalian cells.

The screening by the two-hybrid method can be carried out by using, for example, "MATCHMAKER Two-Hybrid System", "Mammalian MATCHMAKER Two-Hybrid Assay Kit", "MATCHMAKER One-Hybrid System" (each manufactured by TAKARA BIO INC.), or "HybriZAP Two-Hybrid Vector System" (manufactured by Stratagene).

EXAMPLES

Hereinafter, the present invention will be described in more detail. However, the present invention is not limited to these examples.

(1) Analysis of a Single Nucleotide Polymorphism

Japanese patients suffering from myocardial infarction and those not suffering from myocardial infarction (controls), from all of which informed consent has been obtained, were respectively analyzed for single nucleotide polymorphisms in TLR1 gene and TLR4 gene. Specifically, with respect to the polymorphism at nucleotide "1805" of the TLR1 gene, chromosomal DNA isolated from the blood of a subject was used as a template to carry out PCR with primers of SEQ ID NOs: 4 and 5, thereby amplifying DNA fragments. The fragments were digested with restriction enzyme PstI (Takara) and migration patterns thereof obtained by 4% Nusieve GTG agarose gel (Takara) were analyzed for the polymorphism.

For the polymorphism at nucleotide "130" of the TLR1 gene, a chromosomal DNA isolated from the blood of the subject was used as a template to carry out PCR using primers of SEQ ID NOs: 6 and 7. The amplified products were subjected to a sequence analysis of the polymorphic site using a primer of SEQ ID NO: 10.

For the polymorphism at nucleotide "−1440" of the TLR4 gene, a chromosomal DNA isolated from the blood of the subject was used as a template to carry out PCR with primers of SEQ ID NOs: 8 and 9, followed by subjecting the amplified products to a sequence analysis for the polymorphic site using a primer of SEQ ID NO: 11.

Here, the patients with myocardial infarction are those who have been diagnosed as suffering from myocardial infarction by satisfying at least two of the three conditions: (i) having any clinical recording of chest pressure sensation, pain, and oppressive feeling in chest for 30 minutes or more; (ii) showing an increase in ST segment larger than 0.1 mV with one standard lead or two precordial leads; and (iii) showing at least two-fold increase in standard level of serum creatine kinase (Nat Genet. 2002 December; 32 (4): 650-4. 2002).

The results of the SNPs analysis are shown in Table 1.

TABLE 1

Association of SNPs in TLR1 gene with myocardial infarction (MI)

| Genotype | MI: number of subjects (%) | Control: number of subjects (%) | Allele T vs allele C (exon 1) or G (exon 4) | | CC (exon 1) or TT (exon 4) vs others | |
|---|---|---|---|---|---|---|
| | | | $\chi^2$[P value] | Odds ratio(95% CI) | $\chi^2$[P value] | Odds ratio(95% CI) |
| TLR1 exon 1 130T > C* Ser44Pro | | | | | | |
| TT | 2210(86.5%) | 1590(88.7%) | 5.23 | 1.23 | 4.52 | 3.5 |
| TC | 324(12.8%) | 199(11.1%) | [0.022] | (1.03-1.47) | [0.034] | (1.02-12.2) |
| CC | 15(0.6%) | 3(0.2%) | | | | |
| Total | 2649(100%) | 1792(100%) | | | | |
| TLR1 exon 4 1805T > G* Ser602Ile | | | | | | |
| TT | 2685(97.6%) | 2046(99.0%) | 13.4 | 2.52 | 15.95 | 2.72 |
| TG | 66(2.4%) | 20(1.0%) | [0.00021] | (1.52-4.16) | [0.000065] | (1.63-4.53) |
| GG | 0(0%) | 0(0%) | | | | |
| Total | 2751(100%) | 2066(100%) | | | | |

TABLE 2

Comparison between subjects having the combination of CC homozygote of the SNP 130 and TG heterozygote of the SNP 1805 and subjects having other genotypes

|    | Others; number of subjects (%) | combination; number of subjects (%) | $\chi^2$[P value] | Odds ratio(95% CI) |
|----|---|---|---|---|
| MI | 2276 | 68 | 17.12 | 3.01 |
| CO | 1614 | 16 | [0.000035] | [1.74-5.25] |

TABLE 3

Association of SNPs in TLR4 gene with myocardial infarction (MI)

| | | | | | $\chi^2$ [P value] (Odds ratio) < 95% CI> | | |
|---|---|---|---|---|---|---|---|
| Genotype | MI; number of subjects (%) | Control; number of subjects (%) | Genotype frequency | Allele frequency | | TT vs Others | CC vs Others |
| TLR4 promoter-1440 T > C* | | | | | | | |
| TT | 1516(55.0%) | 1287(56.0%) | 12.5 | 9.2 | | 4.5 | 11.1 |
| TC | 1037(37.6%) | 820(37.0%) | [0.0019] | [0.0024] | | [0.034] | [0.00084] |
| CC | 203(7.4%) | 112(5.0%) | | (1.16) | | (1.13) | (1.5) |
| Total | 2756(100%) | 2219(100%) | | <1.05-1.26> | | <1.01-1.26> | <1.18-1.90> |

As is evident from Table 1, with respect to the T/C polymorphism at the nucleotide "130" of the TLR1 gene, the ratio of "C" is significantly high in the patients with myocardial infarction ($\chi^2$=5.23, P=0.0022; odds ratio=1.23). With respect to the T/G polymorphism at the nucleotide "1805" in exon 4 of the TL1 gene, the ratio of "G" is significantly high in the patients with myocardial infarction ($\chi^2$=13.4, P-0.00021; odds ratio=2.52).

Further, when a subject having CC allele at the nucleotide "130" and TG allele at the nucleotide 1805 (combination) was compared with a subject having other alleles (others), it was found that the "combination" subject was significantly high in myocardial infarction (Table 2; $\chi^2$=17.12, P=0.000035; odds ratio=3.01).

Table 3 shows the relationship between the T/C polymorphism at the nucleotide "−1440" in the promoter region of the TLR4 gene and myocardial infarction. Table 3 shows that the ratio of "C" is significantly high in the patient with myocardial infarction ($\chi^2$=9.2, P=0.0024; odds ratio=1.15).

(2) Confirmation of Interaction Between TLR and Galectin-2 Construction of FLAG-Tag-Fused Galectin-2 (Galectin-FLAG)

Primers (SEQ ID NOs: 18 and 19) specific to galectin-2 added with EcoRI and XhoI sites, respectively were used to carry out PCR using human liver cDNA (TAKARA BIO INC.) as a template. The amplified fragment was subjected to EcoRI and XhoI treatment and then inserted to pFLAG-CMV5a vector (SIGMA) similarly treated with EcoRI and XhoI, thereby obtaining a FLAG-tag-fused galectin-2 expression vector (galectin-2-FLAG).

Vectors for HA-tag-fused TLR1, 2, and 3 expression were purchased from InvivoGen (TLR-HA1, 2, and 3).

COS7 cells (Health Science Research Resources Bank; JCRB9127) were transiently transfected with the galectin-2-FLAG expression vector and the TLR-HA expression vector using Fugene (Roche), respectively. After 24 hours, the cells were dissolved for 1 hour or more using a lysis buffer (20 mM Tris-HCl pH7.5, 150 mM NaCl, 0.1% Triton X-100) containing Complete protease inhibitor tablet (Roche; 1 tablet per 20 ml) and MG-132 (Calbiochm; 5 μg/ml) to the extent that insoluble debris is not precipitated. Subsequently, immunoprecipitation was carried out using anti-FLAG-tag M2 agarose (Sigma) or anti-HA agarose (Santacruz) at 4° C. for 12 to 18 hours. The precipitate was washed three times with the lysis buffer and was then visualized using anti-HA-antibody peroxydase conjugate (Santa Cruz) or anti-FLAG-antibody peroxydase conjugate (Sigma). The results are shown in FIG. 1. As a result of western blot (WB) with the HA antibody with respect to the precipitate obtained by immunoprecipitation (IP) using the FLAG antibody, TLR1 and TLR2 were co-precipitated with the galectin-2-FLAG. Consequently, it is evident that TLR1 and TLR2 specifically interact with galectin-2.

(3) Confirmation of Interaction Between Intracellular Domain of TLR2 and Galectin-2

A vector for expressing the intracellular domain of TLR2 (domain of amino acids 614 to 784 of SEQ ID NO: 15) fused with S-tag was constructed. First, primers of SEQ ID NOs: 21 and 22 were used to amplify DNA fragments that encode the intracellular domain of TLR2, followed by insertion into a pTriEx4 vector (Novagen) (S-tag-TLR2ID).

COS7 cells (Health Science Research Resources Bank; JCRB9127) were transiently transfected with the galectin-2-FLAG expression vector and the S-tag-TLR2ID expression vector using Fugene (Roche). After carrying out immunoprecipitation with S-Protein, western blot (WB) was carried out with S-Protein or anti-FLAG antibody. The results showed that the intracellular domain of TLR2 interacted with galectin-2.

INDUSTRIAL APPLICABILITY

According to the diagnosis method of the present invention, inflammatory diseases such as myocardial infarction can be detected at an early stage, which is useful in the fields of diagnosis and the like. Further, according to the screening method of the present invention, novel medicaments for inflammatory diseases such as myocardial infarction can be obtained, which is useful in medical fields and the like.

The invention claimed is:

1. A method for diagnosing an increased risk of myocardial infarction comprising:

analyzing single nucleotide polymorphisms of a Toll-like receptor 1 gene that are polymorphisms of a nucleotide corresponding to the nucleotide at position 201 of SEQ ID NO: 1 or of a nucleotide corresponding to the nucleotide at position 197 of SEQ ID NO: 2, and diagnosing an increased risk of myocardial infarction based on a result of the analysis.

* * * * *